US006348619B1

(12) United States Patent
Yoshida et al.

(10) Patent No.: US 6,348,619 B1
(45) Date of Patent: Feb. 19, 2002

(54) PROCESS FOR PRODUCING A CARBOXYLIC ACID ESTER BY REACTING AN ALDEHYDE AND AN ALCOHOL USING A PALLADIUM TYPE CATALYST

(75) Inventors: Yasukazu Yoshida; Yuji Mikami; Motomu Oh-Kita, all of Otake (JP)

(73) Assignee: Mitsubishi Rayon Co., Ltd., Tokyo (JP)

( * ) Notice: Subject to any disclaimer, the term of this patent is extended or adjusted under 35 U.S.C. 154(b) by 0 days.

(21) Appl. No.: 09/230,355
(22) PCT Filed: Mar. 19, 1998
(86) PCT No.: PCT/JP98/01179
  § 371 Date: Jan. 25, 1999
  § 102(e) Date: Jan. 25, 1999
(87) PCT Pub. No.: WO98/42653
  PCT Pub. Date: Oct. 1, 1998

(30) Foreign Application Priority Data
Mar. 24, 1997 (JP) ............................... 9-069624

(51) Int. Cl.$^7$ ............................... C07C 67/00
(52) U.S. Cl. ......................... 560/210; 560/20
(58) Field of Search ................... 560/20, 216

(56) References Cited

U.S. PATENT DOCUMENTS 4,520,125 A * 5/1985 Baer et al.

FOREIGN PATENT DOCUMENTS

| JP | 54-73715 | | 6/1979 |
| JP | 54-73717 | | 6/1979 |
| JP | 55-153741 | | 11/1980 |
| JP | 5-148184 | | 6/1993 |
| JP | 9-221453 | * | 8/1997 |

* cited by examiner

Primary Examiner—Gary Geist
Assistant Examiner—Robert W. Deemie
(74) Attorney, Agent, or Firm—Oblon, Spivak, McClelland, Maier & Neustadt, P.C.

(57) ABSTRACT

A carboxylic acid ester is prepared by a process comprising:
  reacting an aldehyde and an alcohol in a liquid phase in the presence of molecular oxygen as indicated by the following reaction:

$$RCHO + R'OH + O_2 \rightarrow RCOOR' + H_2O$$

in the presence of a catalyst comprising at least palladium and an element X, wherein X is bismuth, lead or a combination thereof, supported on a carrier, wherein the catalyst has an acid strength, pKa, of more than 4.8 and shows an ammonia chemical adsorption amount at 0° C. of 0–150 μmol/g-catalyst.

12 Claims, No Drawings

PROCESS FOR PRODUCING A CARBOXYLIC ACID ESTER BY REACTING AN ALDEHYDE AND AN ALCOHOL USING A PALLADIUM TYPE CATALYST

TECHNICAL FIELD

The present invention relates to a process for producing a carboxylic acid ester by reacting an aldehyde and an alcohol in a liquid phase in the presence of molecular oxygen by using a catalyst and to a catalyst used for the process.

BACKGROUND ART

Catalysts which have been proposed to be used in a process for producing a carboxylic acid ester from an aldehyde and an alcohol in the presence of molecular oxygen by using a catalyst include, for example, a palladium-lead type catalyst disclosed in JP-B-57-35856, JP-B-4-72578, JP-A-57-50545 and others, a palladium-tellurium type catalyst disclosed in JP-A-61-243044, a palladium-thallium-mercury type catalyst disclosed in JP-B-57-35860, a palladium-alkaline earth metal-zinc-cadmium type catalyst disclosed in JP-B-57-19090, and a palladium-bismuth type catalyst disclosed in JP-B-61-60820, JP-B-62-7902, JP-A-5-148184 and others. As to the carrier of the catalyst used for such processes, there have been proposed, for example, calcium carbonate in JP-B-57-35856 and JP-B-57-35860, zinc oxide-alumina, titania-lanthanum oxide and zinc oxide-titania in JP-B-4-46618, zinc oxide in JP-B-4-72578, a carrier having a specific surface area of not more than 70 m$^2$/g in JP-A-57-50942 and a hydrophobic carrier in JP-A-5-148184.

However, these catalysts are apt to differ in the yield of carboxylic acid esters even when the components and/or the carrier of the catalyst are of the same composition. Therefore, the development of a process, improved in the above-mentioned point, which can produce carboxylic acid esters with a high yield has been eagerly awaited.

DISCLOSURE OF THE INVENTION

The object of the present invention is to provide a process for producing a carboxylic acid ester from an aldehyde and an alcohol with a high yield and a catalyst used for the process.

Thus, the present invention provides a process for producing a carboxylic acid ester, comprising reacting an aldehyde and an alcohol in a liquid phase in the presence of molecular oxygen by the use of a catalyst comprising at least palladium and X (X represents bismuth and/or lead) supported on a carrier, wherein the catalyst used has an acid strength, pKa, of more than 4.8 and shows an ammonia chemical adsorption amount at 0° C. of 0–150 μmol/g-catalyst.

The present invention further provides a catalyst used for producing a carboxylic acid ester by reacting an aldehyde and an alcohol in a liquid phase in the presence of molecular oxygen, which comprises at least palladium and X (X represents bismuth and/or lead) supported on a carrier, has an acid strength, pKa, of more than 4.8 and shows an ammonia chemical adsorption amount at 0° C. of 0–150 μmol/g-catalyst.

In the catalyst and the process according to the present invention, the aldehyde used as a starting material may be, for example, aromatic aldehydes, such as benzaldehyde, methylbenzaldehyde, and nitrobenzaldehyde, saturated aliphatic aldehydes, such as acetaldehyde, propionaldehyde and isobutyl aldehyde, and unsaturated aliphatic aldehydes, such as acrolein, methacrolein and crotonaldehyde. The alcohol of a starting material may be, for example, methanol, ethanol, isopropanol, allyl alcohol and methallyl alcohol.

The catalyst of the present invention and the catalyst used in the process of the present invention comprise palladium, as a catalyst component, supported on a carrier and additionally bismuth and/or lead, as a catalyst component(s), supported on the carrier. The term "catalyst" herein refers not only to the catalyst components supported on a carrier but also to the whole catalyst system including the carrier. A starting material for palladium used in preparing the catalyst may be, for example, palladium acetate, palladium chloride, palladium nitrate, palladium ammonium chloride, and palladium-ammine complex salt, a starting material for bismuth may be, for example, bismuth acetate, bismuth carbonate, bismuth chloride, bismuth nitrate and bismuth sulfate, and a starting material for lead may be, for example, metal compounds, such as lead acetate, lead carbonate, lead chloride, lead nitrate, lead sulfate, lead tartrate and lead citrate. Besides palladium, bismuth and lead, third components, such as chromium, iron, cobalt, zinc, barium and silver, may be supported as catalyst components on the carrier. The catalyst components are present on the carrier in the form of a metal and/or a metal compound.

In the catalyst of the present invention and the catalyst used in the process of the present invention, the amounts of the respective catalyst components to be supported on the carrier are, based on 100 parts by weight of the carrier, preferably 1–15 parts by weight, more preferably 3–13 parts by weight for palladium, and 0.1–15 parts by weight, more preferably 0.5–12 parts by weight for X. When the catalyst component is a metal compound, the above-mentioned amount to be supported is calculated in terms of the weight of the metal atom in the metal compound. The carriers may be for example, calcium carbonate, zinc oxide, silica and silica-magnesia. Average particle diameter and specific surface area of the carrier are, for example, 5–150 μm and 50–200 m$^2$/g, respectively.

The catalyst of the present invention and the catalyst used in the process of the present invention have an acid strength, pKa, of more than 4.8. The acid strength, pKa, herein is an index which indicates the degree of acidity of the surface of a material. It is signified that the larger the value of pKa, the weaker the acidity. The acid strength pKa is determined according to the method described in Shokubai (catalyst), vol. 11 pp. 210–216 (1969) (written by Isao Matsuzaki et al., published by Shokubai Gakkai (Catalyst Society)) by using an indicator which changes its color in a predetermined range of pKa. When a catalyst which has a pKa of not more than 4.8 is used, by-products such as acetals tend to be formed markedly to lower the yield of the carboxylic acid ester of the objective product.

The catalyst of the present invention and the catalyst used in the process of the present invention show an ammonia chemical adsorption amount at 0° C. (hereinafter referred to simply as "ammonia chemical adsorption amount") of 0–150 μmol/g-catalyst, preferably 30–140 μmol/g-catalyst. The term "ammonia chemical adsorption amount" herein refers to the amount of ammonia chemically adsorbed to 1 g of catalyst at 0° C. It is signified that the larger the value of the above-mentioned amount, the larger the amount of acid sites per 1 g of the catalyst (hereinafter referred to as "acid amount"). To determine the ammonia chemical adsorption amount, the total adsorption amount, which is the sum of the chemical adsorption amount and the physical adsorption amount of ammonia, and the physical adsorption amount of ammonia are determined at 0° C. by using a common adsorption-desorption apparatus available on the market, and the "ammonia chemical adsorption amount" can be obtained from the difference of the two amounts determined above. When a catalyst which shows an ammonia chemical adsorption amount of more than 150 μmol/g-catalyst is used, by-products, such as acetals, tend to be formed markedly, to lower the yield of the objective product.

The catalyst of the present invention and the catalyst used in the process of the present invention can be prepared by conventional methods. As an example of the method of preparation, the preparation of a catalyst comprising palladium, bismuth and iron supported on a silica-magnesia carrier is described below. First, palladium chloride, bismuth nitrate and nitric acid are added to water, and the resulting mixture is heated to form a solution. Then, silica-magnesia powder, and thereafter a reducing agent such as formalin are added to the solution, and the resulting mixture is stirred with heating for a predetermined time. Thereafter, the mixture is filtered and the solid obtained is immersed in an aqueous solution of ferric nitrate. In this time, if desired, the solid may be reduced again with a reducing agent to deposit a metal. The solid is again collected by filtration, and then dried to obtain a catalyst. The catalyst obtained may also be activated by conventional methods.

In the present invention, a carboxylic acid ester is produced by reacting an aldehyde and an alcohol in a liquid phase in the presence of molecular oxygen by using a catalyst which has an acid strength, pKa, of more than 4.8 and shows an ammonia chemical adsorption amount of 0–150 μmol/g-catalyst. The molar ratio of the aldehyde to the alcohol of the starting materials is preferably 1:100 to 1:1, more preferably 1:80 to 1:3.

In carrying out the reaction according to the process of the present invention, the catalyst is dispersed as a suspension in the liquid phase. The reaction may be conducted either batch-wise or semibatch-wise or continuously. The source of the molecular oxygen used as the oxidizing agent may be air, oxygen-enriched air, oxygen or the like. The reaction temperature is preferably 0–100° C., more preferably 30–80° C. The reaction may be conducted at ordinary pressure or under applied pressure.

The molecular oxygen is used in an amount sufficient to form the intended carboxylic acid ester. The amount is preferably 10–500 ml/min relative to 100 ml of the reaction liquid. As to a solvent used for forming the liquid phase, for example, the aldehyde and/or the alcohol used in the process of the present invention may be used as such to form the liquid phase, but the solvent is not limited thereto. For example, hexane, acetone, benzene and the like may be used as the solvent. The amount of the catalyst to be used is not particularly limited, and may be, for example, 0.01 g–1 g per 1 g of aldehyde.

BEST MODE FOR CARRYING OUT THE INVENTION

The present invention is described in detail below with reference to Examples and Comparative Examples, but the invention is in no way limited thereto. The "supported amount" of the metal and/or metal compound of the catalyst component refers to the weight of metal atom in the catalyst component, which is a value obtained by calculation from the amount of the starting material used for catalyst preparation. The catalyst composition was expressed by describing, behind the atomic symbol of the catalyst component, a supported amount per 100 parts by weight of the carrier and then, behind the slant line (/), the carrier. The acid strength, pKa, was determined according to the method described in Shokubai, Vol. 11, pp. 210–216 (1969) as mentioned above. The ammonia chemical adsorption amount at 0° C. was determined by using a BET type adsorption measuring apparatus. Analysis of a reaction product was made by means of gas chromatography. Conversion of the aldehyde of the starting material (hereinafter referred to as "conversion"), selectivity to the carboxylic acid ester of the objective product (hereinafter referred to as "ester selectivity"), selectivity to the acetal of by-product (hereinafter referred to as "acetal selectivity") and yield of the carboxylic acid ester of the objective product (hereinafter eferred to as "yield") were calculated according to the following definitions,

| | | |
|---|---|---|
| Conversion (%) | = | B/A × 100 |
| Ester selectivity (%) | = | C/B × 100 |
| Acetal selectivity (%) | = | D/B × 100 |
| Yield (%) | = | C/A × 100 | wherein A, B, C and D respectively represent:
A: the number of moles of fed starting material aldehyde,
B: the number of moles of reacted starting material aldehyde,
C: the number of moles of formed carboxylic acid ester,
D: the number of moles of formed acetal.

EXAMPLE 1

In 50 ml of pure water was dissolved with heating 0.85 g of palladium chloride, 0.46 g of bismuth nitrate and 5 g of a 60 wt % aqueous nitric acid solution, then 10 g of a silica-magnesia powder with an average particle diameter of 100 μm was added to the solution, and the resulting mixture was stirred. To the mixture was added 50 ml of an aqueous solution containing 5 wt % of sodium hydroxide and 5 wt % of formalin, the resulting mixture was stirred at 70° C. for 30 minutes, then filtered, and the resulting cake was washed with water and dried to obtain a catalyst shown in Table 1. In a 300 ml flask fitted with a reflux condenser were placed 2 g of the catalyst obtained above, 4.3 g of benzaldehyde and 80 g of methanol, and the mixture was allowed to react at 50° C. for 2 hours while air was being blown thereinto at a flow rate of 100 ml/min, to obtain methyl benzoate as a carboxylic acid ester. The results thus obtained are shown in Table 2.

EXAMPLE 2

In 50 ml of pure water were dissolved with heating 0.85 g of palladium chloride, 0.46 g of bismuth nitrate and 5 g of a 60 wt % aqueous nitric acid solution, then 10 g of a silica-magnesia powder with an average particle diameter of 100 μm was added to the solution, and the resulting mixture was stirred. To the mixture was added 50 ml of an aqueous solution containing 5 wt % of sodium hydroxide and 5 wt % of formalin, the resulting mixture was stirred at 70° C. for 30 minutes, then filtered, and the resulting cake was washed with water (solid A). The solid A was added to a solution of 0.72 g of ferric nitrate dissolved in 40 ml of pure water, and the mixture was stirred. Then 20 ml of a 5 wt % aqueous formalin solution was added to the mixture, the resulting mixture was filtered, and the cake obtained was washed with water and dried to obtain the catalyst shown in Table 1. A reaction was conducted using the catalyst under the same conditions as in Example 1, to obtain the results shown in Table 2.

EXAMPLE 3

A catalyst was prepared in the same manner as in Example 2 except for using 0.34 g of zinc acetate in place of ferric nitrate, to obtain a catalyst shown in Table 1. The catalyst was used to conduct a reaction under the same conditions as in Example 1, to obtain the results shown in Table 2.

EXAMPLE 4

In 50 ml of pure water were dissolved with heating 0.85 g of palladium chloride, 0.16 g of lead nitrate and 2 g of a 60 wt % aqueous nitric acid solution, then 10 g of a silica-magnesia powder with an average particle diameter of 100 μm was added to the solution, and the resulting mixture was stirred. To the mixture was added 50 ml of an aqueous solution containing 5 wt % of sodium hydroxide and 5 wt % of formalin, the resulting mixture was stirred at 80° C. for 30 minutes, then filtered, and the cake was washed with water and dried, to obtain a catalyst shown in Table 1. The catalyst was used to conduct a reaction under the same conditions as in Example 1, to obtain the results shown in Table 2.

EXAMPLE 5

In 50 ml of pure water were dissolved with heating 0.85 g of palladium chloride, 0.16 g of lead nitrate and 2 g of a 60 wt % aqueous nitric acid solution, then 10 g of a silica-magnesia powder with an average particle diameter of 100 μm was added to the solution, and the resulting mixture was stirred. To the mixture was added 50 ml of an aqueous solution containing 5 wt % of sodium hydroxide and 5 wt % of formalin, the resulting mixture was stirred at 80° C. for 30 minutes, then filtered, and the cake was washed with water and dried (solid A). The solid A was added to an aqueous solution of 0.72 g of ferric nitrate dissolved in 40 ml of pure water and the mixture was stirred. Then 20 ml of a 5 wt % aqueous formalin solution was added to the mixture, the resulting mixture was filtered, and the cake was washed with water and then dried to obtain a catalyst shown in Table 1. The catalyst was used to conduct a reaction under the same conditions as in Example 1, to obtain the results shown in Table 2.

EXAMPLE 6

A catalyst was prepared in the same manner as in Example 5 except for using 0.34 g of zinc acetate in place of ferric nitrate, to obtain a catalyst shown in Table 1. The catalyst was used to conduct a reaction under the same conditions as in Example 1, to obtain the results shown in Table 2.

EXAMPLE 7

A catalyst was prepared in the same manner as in Example 5 except for using 0.72 g of ferric nitrate and 0.17 g of zinc acetate in place of ferric nitrate, to obtain a catalyst shown in Table 1. The catalyst was used to conduct a reaction under the same conditions as in Example 1 to obtain the results shown in Table 2.

EXAMPLE 8

In 50 ml of pure water were dissolved with heating 0.85 g of palladium chloride, 0.16 g of lead nitrate, 0.46 g of bismuth nitrate and 5 g of 60 wt % aqueous nitric acid solution, then 10 g of a silica-magnesia powder with an average particle diameter of 100 μm was added to the solution, and the resulting mixture was stirred. To the mixture was added 80 ml of an aqueous solution containing 5 wt % of sodium hydroxide and 5 wt % of formalin, the resulting mixture was stirred at 70° C. for 30 minutes, then filtered, and the resulting cake was washed with water and dried to obtain a catalyst shown in Table 1. The catalyst was used to conduct a reaction under the same conditions as in Example 1, to obtain the results shown in Table 2.

EXAMPLE 9

In 50 ml of pure water were dissolved with heating 0.85 g of palladium chloride, 0.16 g of lead nitrate, 0.46 g of bismuth nitrate and 5 g of a 60 wt % aqueous nitric acid solution, then 10 g of a silica-magnesia powder with an average particle diameter of 100 μm was added to the solution and the resulting mixture was stirred. To the mixture was added 80 ml of an aqueous solution containing 5 wt % of sodium hydroxide and 5 wt % of formalin, the resulting mixture was stirred at 70° C. for 30 minutes, then filtered, and the resulting cake was washed with water (solid A). The solid A was added to a solution of 0.72 g of ferric nitrate dissolved in 40 ml of pure water and the mixture was stirred. Then 20 ml of a 5 wt % aqueous formalin solution was added to the mixture, the resulting mixture was filtered, and the cake was washed with water and dried to obtain a catalyst shown in Table 1. The catalyst was used to conduct a reaction under the same conditions as in Example 1 to obtain the results shown in Table 2.

EXAMPLE 10

A catalyst was prepared in the same manner as in Example 9 except for using 0.34 g of zinc acetate in place of ferric nitrate, to obtain a catalyst shown in Table 1. The catalyst was used to conduct a reaction under the same conditions as in Example 1, to obtain the results shown in Table 2.

EXAMPLE 11

A catalyst was prepared in the same manner as in Example 9 except for using 0.19 g of barium acetate in place of ferric nitrate and using a silica powder with an average particle diameter of 100 μm in place of silica-magnesia, to obtain a catalyst shown in Table 1. The catalyst was used to conduct a reaction under the same conditions as in Example 1 to obtain the results shown in Table 2.

EXAMPLE 12

A catalyst was prepared in the same manner as in Example 9 except for using 0.42 g of cobalt acetate in place of ferric nitrate and using a silica powder with an average particle diameter of 100 μm in place of silica-magnesia, to obtain a catalyst shown in Table 1. The catalyst was used to conduct a reaction under the same conditions as in Example 1 to obtain the results shown in Table 2.

EXAMPLE 13

A catalyst was prepared in the same manner as in Example 9 except for using a calcium carbonate powder with an average particle diameter of 6 μm in place of silica-magnesia, to obtain a catalyst shown in Table 1. The catalyst was used to conduct a reaction under the same conditions as in Example 1 to obtain the results shown in Table 2.

EXAMPLE 14

A reaction was conducted under the same conditions as in Example 1 except for using the catalyst prepared in Example 2 and using 5.02 g of p-methyl-benzaldehyde as an aldehyde. Methyl p-toluate was obtained as a carboxylic acid ester. The results obtained are shown in Table 2.

EXAMPLE 15

A reaction was conducted under the same conditions as in Example 1 except for using the catalyst prepared in Example 2 and using 6.41 g of p-nitro-benzaldehyde in place of benzaldehyde, to obtain methyl p-nitrobenzoate as a carboxylic acid ester. The results thus obtained are shown in Table 2.

EXAMPLE 16

A reaction was conducted under the same conditions as in Example 1 using the catalyst prepared in Example 1 except for using 2.87 g of methacrolein in place of benzaldehyde and changing a reaction time to 4 hours, to obtain methyl methacrylate as a carboxylic acid ester. The results thus obtained are shown in Table 2.

EXAMPLE 17

A reaction was conducted under the same conditions as in Example 1 except for using the catalyst prepared in Example 2, using 2.87 g of methacrolein in place of benzaldehyde and changing a reaction time to 4 hours, to obtain methyl methacrylate as a carboxylic acid ester. The results thus obtained are shown in Table 2.

EXAMPLE 18

A reaction was conducted under the same conditions as in Example 1 except for using the catalyst prepared in Example 2, using 2.3 g of acrolein in place of benzaldehyde and changing a reaction time to 4 hours, to obtain methyl acrylate as a carboxylic acid ester. The results thus obtained are shown in Table 2.

COMPARATIVE EXAMPLE 1

A catalyst was prepared in the same manner as in Example 1 except for using a titania with an average particle diameter of 100 $\mu$m in place of silica-magnesia, to obtain a catalyst shown in Table 1. The catalyst was used to conduct a reaction under the same conditions as in Example 1. The results thus obtained are shown in Table 2.

COMPARATIVE EXAMPLE 2

A catalyst was prepared in the same manner as in Example 2 except for using a zirconia with an average particle diameter of 50 $\mu$m in place of silica-magnesia, to obtain a catalyst shown in Table 1. The catalyst was used to conduct a reaction under the same conditions as in Example 1, to obtain the results shown in Table 2.

TABLE 1

| | Catalyst composition | Acid strength pKa | Ammonia chemical adsorption amount ($\mu$mol/g-cat) |
|---|---|---|---|
| Example 1 | Pd5—Bi2/SiO2—MgO | pKa > 4.8 | 115.3 |
| Example 2 | Pd5—Bi2—Fe1/SiO2—MgO | pKa > 4.8 | 128.2 |
| Example 3 | Pd5—Bi2—Zn1/SiO2—MgO | pKa > 4.8 | 111.7 |
| Example 4 | Pd5—Pb1/SiO2—MgO | pKa > 4.8 | 130.5 |
| Example 5 | Pd5—Pb1—Fe1/SiO2—MgO | pKa > 4.8 | 120.3 |
| Example 6 | Pd5—Pb1—Zn1/SiO2—MgO | pKa > 4.8 | 106.5 |
| Example 7 | Pd5—Pb1—Fe1—Zn0.5/SiO2—MgO | pKa > 4.8 | 120.6 |
| Example 8 | Pd5—Bi2—Pb1/SiO2—MgO | pKa > 4.8 | 121.0 |
| Example 9 | Pd5—Bi2—Pb1—Fe1/SiO2—MgO | pKa > 4.8 | 107.6 |
| Example 10 | Pd5—Bi2—Pb1—Zn1/SiO2—MgO | pKa > 4.8 | 105.5 |
| Example 11 | Pd5—Bi2—Pb1—Ba1/SiO2 | pKa > 4.8 | 54.1 |
| Example 12 | Pd5—Bi2—Pb1—Co1/SiO2 | pKa > 4.8 | 68.1 |
| Example 13 | Pd5—Bi2—Pb1—Fe1/CaCO2 | pKa > 4.8 | 59.6 |
| Example 14 | Pd5—Bi2—Fe1/SiO2—MgO | pKa > 4.8 | 128.2 |
| Example 15 | Pd5—Bi2—Fe1/SiO2—MgO | pKa > 4.8 | 128.2 |
| Example 16 | Pd5—Bi2/SiO2—MgO | pKa > 4.8 | 115.3 |
| Example 17 | Pd5—Bi2—Fe1/SiO2—MgO | pKa > 4.8 | 128.2 |
| Example 18 | Pd5—Bi2—Fe1/SiO2—MgO | pKa > 4.8 | 128.2 |
| Comparative Example 1 | Pd5—Bi2—Fe1/TiO2 | 4.0 < pKa ≦ 4.8 | 292.8 |
| Comparative Example 2 | Pd5—Bi2—Fe1/ZrO2 | 4.0 < pKa ≦ 4.8 | 177.4 |

TABLE 2

| | Aldehyde | Alcohol | Conversion (%) | Ester selectivity (%) | Acetal selectivity (%) | Yield (%) |
|---|---|---|---|---|---|---|
| Example 1 | Benzaldehyde | Methanol | 91.1 | 92.5 | 2.2 | 84.3 |
| Example 2 | Benzaldehyde | Methanol | 93.3 | 95.2 | 1.2 | 88.8 |
| Example 3 | Benzaldehyde | Methanol | 91.0 | 93.3 | 2.5 | 84.9 |
| Example 4 | Benzaldehyde | Methanol | 90.2 | 92.7 | 3.2 | 83.6 |
| Example 5 | Benzaldehyde | Methanol | 90.2 | 90.8 | 2.9 | 81.9 |
| Example 6 | Benzaldehyde | Methanol | 87.8 | 90.3 | 3.1 | 79.3 |
| Example 7 | Benzaldehyde | Methanol | 90.1 | 93.5 | 2.9 | 84.2 |
| Example 8 | Benzaldehyde | Methanol | 93.1 | 92.6 | 2.6 | 86.2 |

TABLE 2-continued

|  | Aldehyde | Alcohol | Conversion (%) | Ester selectivity (%) | Acetal selectivity (%) | Yield (%) |
|---|---|---|---|---|---|---|
| Example 9 | Benzaldehyde | Methanol | 94.3 | 95.8 | 1.1 | 90.3 |
| Example 10 | Benzaldehyde | Methanol | 93.3 | 94.5 | 1.5 | 88.2 |
| Example 11 | Benzaldehyde | Methanol | 91.5 | 93.6 | 1.3 | 85.6 |
| Example 12 | Benzaldehyde | Methanol | 94.1 | 94.2 | 1.0 | 88.6 |
| Example 13 | Benzaldehyde | Methanol | 89.1 | 92.8 | 2.0 | 82.7 |
| Example 14 | p-Methylbenzaldehyde | Methanol | 97.8 | 93.7 | 2.1 | 91.6 |
| Example 15 | p-Nitrobenzaldehyde | Methanol | 69.0 | 90.8 | 3.5 | 62.7 |
| Example 16 | Methacrolein | Methanol | 88.0 | 96.8 | 0.31 | 85.2 |
| Example 17 | Methacrolein | Methanol | 85.0 | 95.7 | 0.53 | 81.3 |
| Example 18 | Acrolein | Methanol | 95.0 | 96.3 | 0.42 | 91.5 |
| Comparative Example 1 | Benzaldehyde | Methanol | 97.2 | 0 | 98.0 | 0 |
| Comparative Example 2 | Benzaldehyde | Methanol | 92.9 | 0 | 90.8 | 0 |

INDUSTRIAL APPLICABILITY

According to the process of the present invention, carboxylic acid esters can be produced with a high yield from aldehydes and alcohols.

What is claimed is:

1. A process for producing a carboxylic acid ester, comprising:
    reacting an aldehyde and an alcohol in a liquid phase in the presence of molecular oxygen in the presence of a catalyst comprising at least palladium and an element X, wherein X is bismuth, lead or a combination thereof, supported on a carrier selected from the group consisting of calcium carbonate, silica and silica-magnesia, wherein the catalyst has an acid strength, pKa, of more than 4.8 and shows an ammonia chemical adsorption amount at 0° C. of 0–150 $\mu$mol/g-catalyst.

2. The process according to claim 1 wherein the alcohol is methanol, ethanol, isopropanol, allyl alcohol, methallyl alcohol, or a mixture thereof.

3. The process according to claim 1 wherein the alcohol is methanol.

4. The process according to claim 1 wherein the aldehyde is benzaldehyde, methylbenzaldehyde, nitrobenzaldehyde, acetaldehyde, propionaldehyde, isobutyl aldehyde, acrolein, methacrolein, crotonaldehyde, or a mixture thereof.

5. The process according to claim 1 wherein the aldehyde is benzaldehyde, methylbenzaldehyde, nitrobenzaldehyde, acrolein, methacrolein, or a mixture thereof.

6. The process according to claim 1 wherein the ammonia chemical adsorption amount is 30–140 $\mu$mol/g-catalyst.

7. The process according to claim 1, wherein said ammonia chemical absorption amount is 30–140 $\mu$mol/g-catalyst.

8. The process according to claim 1, wherein the said aldehyde and alcohol react in a molar ratio ranging from 1:100 to 1:1.

9. The process according to claim 1, wherein the reaction is conducted at a temperature ranging from 0–100° C.

10. The process according to claim 1, wherein the amount of molecular oxygen in the reaction ranges from 10–500 ml/min per 100 ml of reaction liquid.

11. The process according to claim 1, wherein the carrier has an average particle diameter and a specific surface area of 5–150 $\mu$m and 50–200 m$^2$/g, respectively.

12. The process according to claim 1, wherein the amounts of catalytically active components of the catalyst, based on 100 parts by wt of the carrier, range from 1–15 parts by wt of Pd and from 0.1–15 parts by wt of element X.

* * * * *